(12) United States Patent
Bezemer et al.

(10) Patent No.: US 6,685,957 B1
(45) Date of Patent: Feb. 3, 2004

(54) PREPARATION OF FIBROUS POLYMER IMPLANT CONTAINING BIOACTIVE AGENTS USING WET SPINNING TECHNIQUE

(75) Inventors: Jeroen Mattijs Bezemer, Utrecht (NL); Clemens Antoni van Blitterswijk, Hekendorp (NL); Jan Feijen, Hengelo (NL); Dirk Wybe Grijpma, Enschede (NL)

(73) Assignee: Chienna B.V., Bilthoven (NL)

( * ) Notice: Subject to any disclaimer, the term of this patent is extended or adjusted under 35 U.S.C. 154(b) by 0 days.

(21) Appl. No.: 09/676,648

(22) Filed: Sep. 29, 2000

(30) Foreign Application Priority Data

Sep. 30, 1999 (EP) .............................. 99203195

(51) Int. Cl.$^7$ ........................... A61F 2/00; A61K 38/00; A61K 38/43; C12N 11/04; C07K 17/04
(52) U.S. Cl. ..................... 424/426; 424/444; 424/94.1; 435/182; 514/2; 530/817
(58) Field of Search ................ 435/174, 177, 435/180, 182, 395; 514/2, 810, 815, 817; 424/426, 94.1, 444

(56) References Cited

U.S. PATENT DOCUMENTS

| | | | | |
|---|---|---|---|---|
| 4,576,817 A | * | 3/1986 | Montgomery et al. | 424/94 |
| 5,096,585 A | * | 3/1992 | Nguyen | 240/500.23 |
| 5,151,227 A | * | 9/1992 | Nguyen et al. | 264/41 |

FOREIGN PATENT DOCUMENTS

| EP | 0 830 859 | 3/1998 |
|---|---|---|
| EP | 0 891 783 A1 | 1/1999 |

OTHER PUBLICATIONS van de Witte et al., "Formation of porous membranes for drug delivery systems," *J. Controlled Release*, 24:61–78 (1993).

* cited by examiner

*Primary Examiner*—David M. Naff
(74) *Attorney, Agent, or Firm*—Banner & Witcoff, Ltd.

(57) ABSTRACT

A fibrous polymer implant loaded with one or more bioactive agents is prepared using a wet spinning technique. Preferably, an aqueous solution of bioactive agent is added to a solution of amphiphilic block copolymer containing hydrophilic blocks such as polyalkylene glycol and hydrophobic blocks such as an aromatic ester dissolved in a first solvent immiscible with water to form an emulsion. The emulsion is injected through a nozzle into a second solvent miscible with the first solvent in which the copolymer is essentially insoluble to form a solid copolymer fiber loaded with the bioactive agent. The fiber is shaped into an implant. Water content of the aqueous solution of bioactive agent affects rate of release of the bioactive agent in vivo. Bioactive agents include peptides, oligopeptides, polypeptides and proteins. The implant may be used as a carrier for controlled drug release or as a scaffold for tissue engineering.

7 Claims, 7 Drawing Sheets

PREPARATION OF FIBROUS POLYMER IMPLANT CONTAINING BIOACTIVE AGENTS USING WET SPINNING TECHNIQUE

BACKGROUND OF THE INVENTION

1. Field of the Invention

The invention relates to a fibrous polymer loaded with one or more bioactive agents and to a process for preparing the fibrous polymer loaded with the bioactive agent or agents. The invention further relates to the use of the polymer loaded with the bioactive agent or agents as a scaffold for tissue engineering.

2. Description of the Related Art

The development of biological substitutes, that can restore or improve tissue function, is a rapidly evolving interdisciplinary field in science. New tissues can be engineered from living cells and three dimensional scaffolds. The function of the scaffold is to provide structural integrity and space for growing tissue, and to guide tissue formation. For this purpose, scaffolds are needed with a high porosity and a high surface area. Ideally, the scaffold delivers bioactive factors which modulate cellular behavior such as proliferation, migration and adhesion. For example, it has been shown that release of bone morphogenetic protein (rhBMP-2) from biodegradable porous scaffolds stimulated growth of bone into the scaffolds in vivo (see K. Whang et al., J. Biomed. Mater. Res. 42 (1998) 491–499).

Macroporous scaffolds for tissue engineering have been fabricated by various techniques, including fiber bonding (see A. G. Mikos et al., J. Biomed. Mater. Res. 27 (1993) 183–189), solvent casting/salt-leaching (see A. G. Mikos et al., Biomaterials 14 (1993) 323–330), phase separation (see H. Lo et al., J. Biomed. Mater. Res. 30 (1996) 475–484) and emulsion freeze-drying (see K. Whang et al., Polymer 36 (1995) 837–842). Often, the methods used to prepare macroporous structures are not suitable for incorporation of labile proteins and other bioactive compounds, due to the high temperatures used, exposure to organic solvents, or the need for removal of the porogens.

Recently, Whang et al. (see J. Biomed. Mater. Res. 42 (1998) 491–499) developed an emulsion freeze-drying process to overcome these drawbacks in the incorporation of proteins into porous matrices. This method consists of creating an emulsion from a poly(lactide-co-glycolide) (PLG) solution in methylene chloride and an aqueous protein solution. Subsequently, the emulsion is quenched in liquid nitrogen, and methylene chloride and water are removed by freeze-drying. The large pores in the resulting matrices are formed by the dispersed water phase and since the proteins are also dissolved in the water phase, this implies that the proteins are located within the large interconnected pores. This might limit the possibilities to obtain slow release of proteins. Furthermore, it appeared that the type of protein influenced the ultimate structure of the pores. In case of bovine serum albumin (BSA) loaded scaffolds, the median pore size was 65 μm, while incorporation of rhBMP-2 resulted in a median pore size of only 9 μm, which is probably too small for optimal bone-ingrowth.

The present invention aims to provide a method for preparing a fibrous polymer loaded with one or more bioactive agents. Further, in particular in view of the application of polymers as scaffold for tissue engineering, it is often desired to be able to incorporate (bioactive) additives in a solid body that constitutes the scaffold. For instance, the presence of growth factors may be very much desired in order to enhance cell growth or differentiation. As many of these bioactive additives are very sensitive compounds, the need for working under mild conditions becomes even more important. It is particularly desired that the method can be performed under such mild conditions that the biologic activity of the bioactive agent is essentially not deteriorated during the carrying out of the method. Further, it is desired that the bioactive agent can be homogeneously distributed throughout the polymer.

SUMMARY OF THE INVENTION

Surprisingly, it has now been found that a wet spinning technique is highly suitable for achieving the above goals. Accordingly, the invention specifically relates to a process for preparing a polymer loaded with one or more bioactive agents comprising the steps of:

a) providing a solution of the polymer in a suitable first solvent;

b) adding an aqueous solution of the bioactive agent or agents to the polymer solution to obtain a water-in-oil emulsion;

c) immersing the water-in-oil emulsion in a suitable second solvent by injecting the emulsion through a nozzle into the second solvent;

d) allowing the first solvent to migrate into the second solvent to obtain a solid, fibrous polymer loaded with the bioactive agent or agents.

DETAILED DESCRIPTION OF THE INVENTION

Figure 1A:
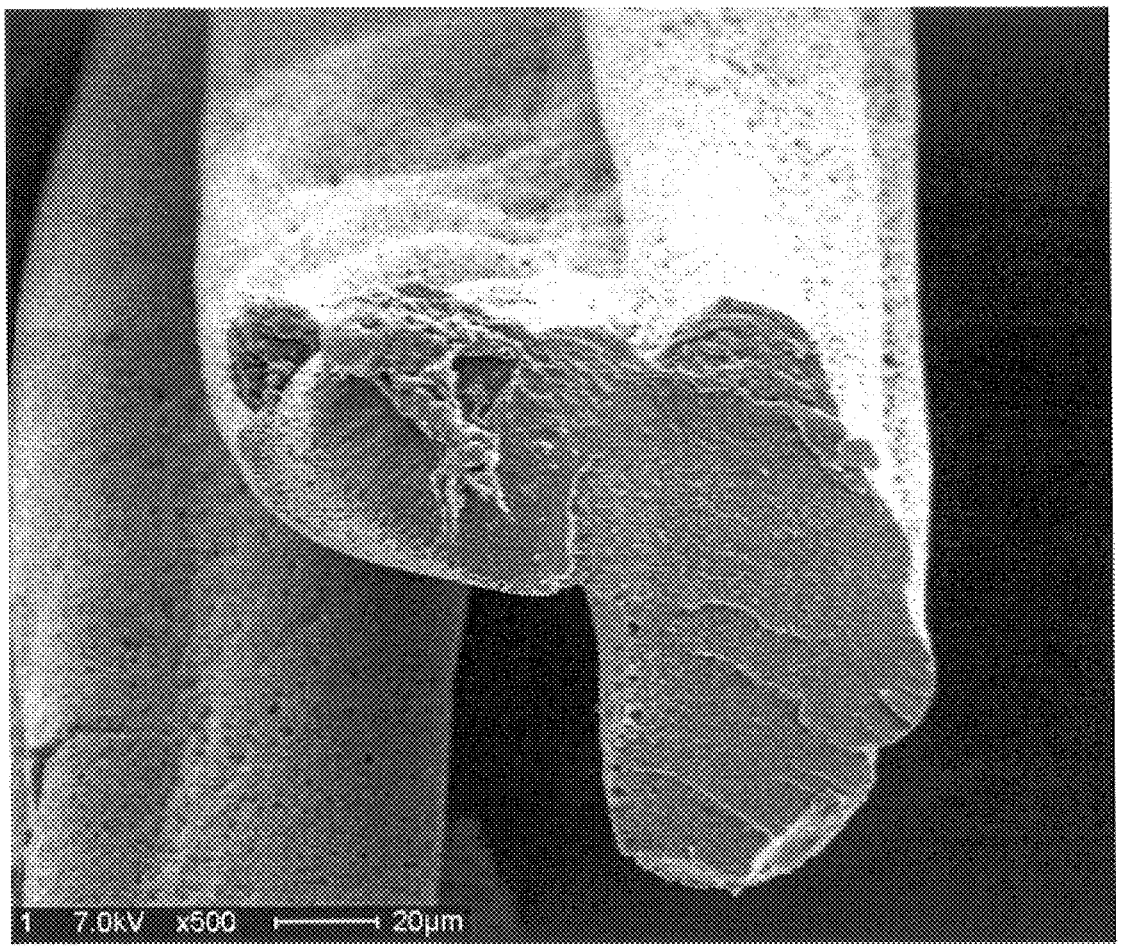
FIGS. 1A and 1B depict scanning electron micrographs of a cross-section of protein loaded PEG/PBT fibers. (A) depicts 500× magnification and (B) depicts 2000× magnification.

The present process is carried out under mild conditions; no high temperatures or extreme pH is required. As a result, the stability and activity of the bioactive agent or agents is essentially maintained during the process. Furthermore, it has been found possible in a process according to the invention to obtain a polymeric substrate in which the bioactive agent is homogeneously distributed. Another advantage is that the present process yields a fibrous product, which is believed to be a highly suitable form for scaffolds in tissue engineering, enabling diffusion of nutrients and waste materials to and from cells seeded on the scaffold and mimicking natural fibrous tissues, such as muscle tissue. Furthermore the present product may find advantageous application in the field of surgical devices and aids, for instance as device for controlled release of bioactive agents in vivo. Specific examples of such devices are spacers that may be used to release an antibiotic, such as gentamycin, in case of an infection, for example when a revision hip implant is to be inserted in a patient, or devices for the release of anti-conception agents.

The polymer which is loaded according to the present invention may be any kind of polymer. Preferably, the polymer is a biocompatible polymer, thus enabling the use of the polymer, loaded with the bioactive agent, for pharmaceutical and/or biological purposes. In the context of the present invention, the term biocompatible is intended to refer to materials which may be incorporated into a human or animal body substantially without unacceptable responses of the human or animal. It is further preferred that the polymer is a biodegradable polymer, which makes the polymer loaded with bioactive agent(s) highly suitable for use as a scaffold in tissue engineering. The term biodegradable refers to materials which, after a certain period of time, are broken down in a biological environment. Preferably, the rate of breakdown is chosen similar or identical to the rate at which the body generates autogenous tissue to replace an implant manufactured of the biodegradable material.

Suitable examples of polymers to be loaded with one or more bioactive agents in accordance with the invention are amphiphilic block copolymers, comprising hydrophilic and hydrophobic blocks. The hydrophilic component is preferably a polyalkylene glycol, such as polyethylene glycol. The hydrophobic blocks may be chosen from a variety of possibilities, including poly(lactide-co-glycolide), poly(caprolactone), polybutylene terephtalate, poly(propylene fumarate), and poly(anhydrides). Such block copolymers may be diblock, triblock, multiblock or star-shaped block copolymers. It has been found that the use of these polymers lead to very stable emulsions, which beneficially affects the formation of the polymer fibers.

A preferred class of polymers according to the invention, is a copolymer of a polyalkylene glycol terephtalate and an aromatic polyester. Preferably, the copolymer comprises 20–90 wt. %, more preferably 40–70 wt. % of the polyalkylene glycol terephtalate, and 80–10 wt. %, more preferably 60–30 wt. % of the aromatic polyester. A preferred type of copolymers according to the invention is formed by the group of block copolymers.

The polyalkylene glycol terephtalate may have a weight average molecular weight of about 150 to about 4000. Preferably, the polyalkylene glycol terephtalate has a weight average molecular weight of 200 to 1500. The aromatic polyester preferably has a weight average molecular weight of from 200 to 5000, more preferably from 250 to 4000. The weight average molecular weight of the copolymer preferably lies between 10,000 and 300,000, more preferably between 40,000 and 120,000.

The weight average molecular weight may suitably be determined by gel permeation chromatography (GPC). This technique, which is known per se, may for instance be performed using chloroform as a solvent and polystyrene as external standard. Alternatively, a measure for the weight average molecular weight may be obtained by using viscometry (see NEN-EN-ISO 1628-1). This technique may for instance be performed at 25° C. using chloroform as a solvent. Preferably, the intrinsic viscosity of the copolymer lies between 0.2289 and 1.3282 dL/g, which corresponds to a weight average molecular weight between 10,000 and 200,000. Likewise, the more preferred ranges for the weight average molecular weight measured by GPC mentioned above can also be expressed in terms of the intrinsic viscosity.

In a preferred embodiment, the polyalkylene glycol terephtalate component has units of the formula —OLO—CO—Q—CO—, wherein O represents oxygen, C represents carbon, L is a divalent organic radical remaining after removal of terminal hydroxyl groups from a poly(oxyalkylene)glycol, and Q is a divalent organic radical.

Preferred polyalkylene glycol terephtalates are chosen from the group of polyethylene glycol terephtalate, polypropylene glycol terephtalate, and polybutylene glycol terephtalate and copolymers thereof, such as poloxamers. A highly preferred polyalkylene glycol terephtalate is polyethylene glycol terephtalate.

The terms alkylene and polyalkylene generally refer to any isomeric structure, i.e. propylene comprises both 1,2-propylene and 1,3-propylene, butylene comprises 1,2-butylene, 1,3-butylene, 2,3-butylene, 1,2-isobutylene, 1,3-isobutylene and 1,4-isobutylene (tetramethylene) and similarly for higher alkylene homologues. The polyalkylene glycol terephtalate component is preferably terminated with a dicarboxylic acid residue —CO—Q—CO—, if necessary to provide a coupling to the polyester component. Group Q may be an aromatic group having the same definition as R, or may be an aliphatic group such as ethylene, propylene, butylene and the like.

The polyester component preferably has units —O—E—O—CO—R—CO—, wherein O represents oxygen, C represents carbon, E is a substituted or unsubstituted alkylene or oxydialkylene radical having from 2 to 8 carbon atoms, and R is a substituted or unsubstituted divalent aromatic radical.

In a preferred embodiment, the polyester is chosen from the group of polyethylene terephthalate, polypropylene terephthalate, and polybutylene terephthalate. A highly preferred polyester is polybutylene terephthalate.

The preparation of the copolymer will now be explained by way of example for a polyethylene glycol terephtalate/polybutylene terephthalate copolymer. Based on this description, the skilled person will be able to prepare any desired copolymer within the above described class. An alternative manner for preparing polyalkylene glycol terephtalate/polyester copolymers is disclosed in U.S. Pat. No. 3,908,201.

A polyethylene glycol terephtalate/polybutylene terephthalate copolymer may be synthesized from a mixture of dimethyl terephthalate, butanediol (in excess), polyethylene glycol, an antioxidant and a catalyst. The mixture is placed in a reaction vessel and heated to about 180° C., and methanol is distilled as transesterification proceeds. During the transesterification, the ester bond with methyl is replaced with an ester bond with butylene and/or the polyethyene glycol. After transesterification, the temperature is raised slowly to about 245° C., and a vacuum (finally less than 0.1 mbar) is achieved. The excess butanediol is distilled off and a prepolymer of butanediol terephthalate condenses with the polyethylene glycol to form a polyethylene/polybutylene terephthalate copolymer. A terephthalate moiety connects the polyethylene glycol units to the polybutylene terephthalate units of the copolymer and thus such a copolymer also is sometimes referred to as a polyethylene glycol terephthalate/polybutylene terephthalate copolymer (PEGT/PBT copolymer).

The bioactive agent which is to be loaded into the polymer may be chosen from various groups of compounds. The term "biologically active agent" or bioactive agent, as used herein, includes an agent which provides a therapeutic or prophylactic effect, a compound that affects or participates in tissue growth, cell growth, cell differentiation, a compound that may be able to invoke a biological action such as an immune response, or could play any other role in one or more biological processes. Such agents include, but are not limited to, antimicrobial agents (including antibacterial and anti-fungal agents), anti-viral agents, anti-tumor agents, hormones, immunogenic agents, growth factors, lipids, lipopolysaccharides, and peptides, polypeptides and proteins in general.

An important group of compounds that can be used for loading a polymer according to the invention is formed by peptides and proteins, of which in principle any kind may be incorporated according to the present invention. Both peptides and proteins are compounds that are built up. out of amino acids, linked to one another via an amide bond (or peptide bond). This bond is the product of the joining of an amino group of one amino acid with a carboxylic acid group of the other. Relatively small peptides may be referred to by the number of amino acids (e.g. di-, tri-, tetrapeptides). A peptide with a relatively small number of amide bonds may also be called an oligopeptide, whereas a peptide with a relatively high number may be called a polypeptide or protein. In addition to being a polymer of amino acid residues, certain proteins may further be characterized by the so called quaternary structure, a conglomerate of a number of polypeptides that are not necessarily chemically linked by amide bonds but are bonded by forces generally known to the skilled professional, such as electrostatic forces and vanderwaals forces. The term peptides, proteins or mixtures thereof as used herein is to include all above mentioned possibilities.

Usually, the protein and/or peptide will be selected on the basis of its biological activity. Depending on the type of polymer chosen, the product obtainable by the present process is highly suitable for controlled release of proteins and peptides. In a preferred embodiment, the protein or peptide is a growth factor. A growth factor is defined as a protein or peptide that has a beneficial effect on the growth, proliferation and/or differentiation of living cells. According to this embodiment, the process of the invention provides a material that can advantageously be used as a scaffold for tissue engineering, wherein the growth factor is released from the polymer in a delayed manner, thus providing a beneficial environment for tissue to grow and/or differentiate.

Examples of preferred growth factors are Bone Morphogenetic Proteins (BMP), epidermal growth factors, e.g. Epidermal Growth Factor (EGF), fibroblast growth factors, e.g. basic Fibroblast Growth Factor (bFGF), Nerve Growth Factor (NGF), Bone Derived Growth Factor (BDGF), transforming growth factors, e.g. Transforming Growth Factor-β1 (TGF-β1), and human Growth Hormone (hGH).

Further examples of peptides or proteins or entities comprising peptides or proteins which may advantageously be contained in the loaded polymer include, but are not limited to, immunogenic peptides or immunogenic proteins, which include, but are not limited to, the following:

1. Toxins: diphtheria toxin, tetanus toxin
2. Viral surface antigens or parts of viruses: adenoviruses, Epstein-Barr Virus, Hepatitis A Virus, Hepatitis B Virus, Herpes viruses, HIV-1, HIV-2, HTLV-III, Influenza viruses, Japanese encephalitis virus, Measles virus, Papilloma viruses, Paramyxoviruses, Polio Virus, Rabies, Virus, Rubella Virus, Vaccinia (Smallpox) viruses, Yellow Fever Virus
3. Bacterial surface antigens or parts of bacteria: *Bordetella pertussis, Helicobacter pylorn, Clostridium tetani, Corynebacterium diphtheria, Escherichia coli, Haemophilus influenza*, Klebsiella species, *Legionella pneumophila, Mycobacterium bovis, Mycobacterium leprae, Mycobacterium tuberculosis, Neisseria gonorrhoeae, Neisseria meningitidis*, Proteus species, *Pseudomonas aeruginosa*, Salmonella species, Shigella species, *Staphylococcus aureus, Streptococcus pyogenes, Vibrio cholera, Yersinia pestis*
4. Surface aintigens of parasites causing disease or portions of parasites: *Plasmodium vivax*—malaria, *Plasmodium falciparum*—malaria, *Plasmodium ovale*—malaria, *Plasmodium malariae*—malaria, *Leishmania tropica*—leishmaniasis, *Leishmania donovani*, leishmaniasis, *Leishmania branziliensis*—leishmaniasis, *Trypanosoma rhodescense*—sleeping sickness, *Trypanosoma gambiense*—sleeping sickness, *Trypanosoma cruzi*—Chagas' disease, *Schistosoma mansoni*—schistosomiasis, *Schistosomoma haematobium*—schistomiasis, *Schistosoma japonicum*—shichtomiasis, *Trichinella spiralis*—trichinosis, *Stronglyloides duodenale*—hookworm, *Ancyclostoma duodenale*—hookworm, *Necator americanus*—hookworm, *Wucheria bancrofti*—filariasis, *Brugia malaya*—filariasis, *Loa loa*—filariasis, *Dipetalonema perstaris*—filariasis, *Dracuncula medinensis*—filariasis, *Onchocerca volvulus*—filariasis
5. Immunoglobulins: IgG, IgA, IgM, Antirabies immunoglobulin, Antivaccinia immunoglobulin
6. Antitoxins: Botulinum antitoxin, diphtheria antitoxin, gas gangrene antitoxin, tetanus antitoxin.
7. Antigens which elicit an immune response against: Foot and Mouth Disease, hormones and growth factors such as follicle stimulating hormone, prolactin, angiogenin, epidermal growth factor, calcitonin, erythropoietin, thyrotropic releasing hormone, insulin, growth hormones, insulin-like growth factors 1 and 2, skeletal growth factor, human chorionic gonadotropin, luteinizing hormone, nerve growth factor, adrenocorticotropic hormone (ACTH), luteinizing hormone releasing hormone (LHRH), parathyroid hormone (PTH), thyrotropin releasing hormone (TRH), vasopressin, cholecystokinin, and corticotropin releasing hormone; cytokines, such as interferons, interleukins, colony stimulating factors, and tumor necrosis factors: fibrinolytic enzymes, such as urokinase, kidney plasminogen activator; and clotting factors, such as Protein C, Factor VIII, Factor IX, Factor VII and Antithrombin III.
8. Examples of other proteins or peptides: albumin, atrial natriuretic factor, renin, superoxide dismutase, $\alpha_1$-antitrypsin, lung surfactant proteins, bacitracin, bestatin, cydosporine, delta sleep-inducing peptide (DSIP), endorphins, glucagon, gramicidin, melanocyte inhibiting factors, neurotensin, oxytocin, somostatin, terprotide, serum thymide factor, thymosin, DDAVP, dermorphin, Met-enkephalin, peptidoglycan, satietin, thymopentin, fibrin degradation product, desenkephalin-α-endorphin, gonadotropin releasing hormone, leuprolide, α-MSH, and metkephamid.

It is to be understood, however, that the scope of the present invention is not limited to any specific peptides or proteins.

Although, in view of the delicacy of proteins and peptides, the present process is particularly useful for making polymers loaded with proteins and peptides, it is of course also possible to load a polymer with a substance other than a protein or peptide. Such biologically active agents which may be incorporated include, but are not limited to, non-peptide, non-protein drugs. It is possible within the scope of the present invention to incorporate drugs of a polymeric nature, but also to incorporate drugs of a relatively small molecular weight of less than 1500, or even less than 500.

Examples of non-peptide, non-protein drugs which may be incorporated include, but are not limited to, the following:

1. Anti-tumor agents: altretamin, fluorouracil, amsacrin, hydroxycarbamide, asparaginase, ifosfamid, bleomycin, lomustin, busulfan, melphalan, chlorambucil, mercaptopurin, chlormethin, methotrexate, cisplatin, mitomycin, cyclophosphamide, procarbazin, cytarabin, teniposid, dacarbazin, thiotepa, dactinomycin, tioguanin, daunorubicin, treosulphan, doxorubicin, tiophosphamide, estramucin, vinblastine, etoglucide, vincristine, etoposid, vindesin.
2. Antimicrobial agents
2.1 Antibiotics
   Penicillins: ampicillin, nafcillin, amoxicillin, oxacillin, azlocillin, penicillin G, carbenicillin, penicillin V, dicloxacillin, phenethicillin, floxacillin, piperacillin, mecillinam, sulbenicillin, methicillin, ticarcillin, mezlocillin
   Cephalosporins: cefaclor, cephalothin, cefadroxil, cephapirin, cefamandole, cephradine, cefatrizine, cefsulodine, cefazolin, ceftazidim, ceforanide, ceftriaxon, cefoxitin, cefuroxime, cephacetrile, latamoxef, cephalexin
   Aminoglycosides: amikacin, neomycin, dibekacyn, kanamycin, gentamycin, netilmycin, kanamycin, tobramycin
   Macrolides: amphotericin B, novobiocin, bacitracin, nystatin, clindamycin, polymyxins, colistin, rovamycin, erythromycin, spectinomycin, lincomycin, vancomycin
   Tetracyclines: chlortetracycline, oxytetracycline, demeclocycline, rolitetracycline, doxycycline, tetracycline, minocycline
   Other antibiotics: chloramphenicol, rifamycin, rifampicin, thiamphenicol
2.2 Chemotherapeutic agents
   Sulfonamides: sulfadiazine, sulfamethizol, sulfadimethoxin, sulfamethoxazole, sulfadimidin, sulfamethoxypyridazine, sulfafurazole, sulfaphenazol, sulfalene, sulfisomidin, sulfamerazine, sulfisoxazole, trimethoprim with sulfamethoxazole or sulfametrole
   Urinary tract antiseptics: methanamine, quinolones (norfloxacin, cinoxacin), nalidixic acid, nitro-compounds (nitrofurantoine, nifurtoinol), oxolinic acid
   Anaerobic infections: metronidazole
3. Drugs for tuberculosis: aminosalicyclic acid, isoniazide, cycloserine, rifampicine, ethambutol, tiocarlide, ethionamide, viomycin
4. Drugs for leprosy: amithiozone, rifampicine, clofazimine, sodium sulfoxone, diaminodiphenylsulfone (DDS, dapsone)
5. Antifungal agents: amphotericin B, ketoconazole, clotrimazole, miconazole, econazole, natamycin, flucytosine, nystatine, griseofulvin
6. Antiuiral agents: aciclovir, idoxuridine, amantidine, methisazone, cytarabine, vidarabine, ganciclovir
7. Chemotherapy of amebiasis: chloroquine, iodoquinol, clioquinol, metronidazole, dehydroemetine, paromomycin, diloxanide, furoatetinidazole, emetine
8. Anti-malarial agents: chloroquine, pyrimethamine, hydroxychloroquine, quinine, mefloquine, sulfadoxine/pyrimethamine, pentamidine, sodium suramin, primaquine, trimethoprim, proguanil
9. Ainti-helmninthiasis agents: antimony potassium tartrate, niridazole, antimony sodium dimercaptosuccinate, oxamniquine, bephenium, piperazine, dichlorophen, praziquantel, diethylcarbamazine, pyrantel parmoate, hycanthone, pyrivium pamoate, levamisole, stibophen, mebendazole, tetramisole, metrifonate, thiobendazole, niclosamide
10. Anti-inflammatory ageints: acetylsalicyclic acid, mefenamic acid, aclofenac, naproxen, azopropanone, niflumic acid, benzydamine, oxyphenbutazone, diclofenac, piroxicam, fenoprofen, pirprofen, flurbiprofen, sodium salicyclate, ibuprofensulindac, indomethacin, tiaprofenic acid, ketoprofen, tolmetin
11. Anti-gout agents: colchicine, allopurinol
12. Centrally acting (opoid) analgesics: alfentanil, methadone, bezitramide, morphine, buprenorfine, nicomorphine, butorfanol, pentazocine, codeine, pethidine, dextromoramide, piritranide, dextropropoxyphene, sufentanil, fentanyl
13. Local anesthetics: articaine, mepivacaine, bupivacaine, prilocaine, etidocaine, procaine, lidocaine, tetracaine
14. Drugs for Parkinson's disease: amantidine, diphenhydramine, apomorphine, ethopropazine, benztropine mesylate, lergotril, biperiden, levodopa, bromocriptine, lisuride, carbidopa, metixen, chlorphenoxamine, orphenadrine, cycrimine, procyclidine, dexetimide, trihexyphenidyl
15. Centrally active muscle relaxants: baclofen, carisoprodol, chlormezanone, chlorzoxazone, cyclobenzaprine, dantrolene, diazepam, febarbamate, mefenoxalone, mephenesin, metoxalone, methocarbamol, tolperisone
16. Hormones and hormone antagonistics
16.1 Corticosteroids
16.1.1 Mineralocorticosteroids: cortisol, desoxycorticosterone, flurohydrocortisone
16.1.2 Glucocorticosteroids: beclomethasone, betamethasone, cortisone, dexamethasone, fluocinolone, fluocinonide, fluocortolone, fluorometholone, fluprednisolone, flurandrenolide, halcinonide, hydrocortisone, medrysone, methylprednisolone, paramethasone, prednisolone, prednisone, triamcinolone (acetonide)
16.2 Androgeins
16.2.1 Androgenic steroids used in therapy: danazole, fluoxymesterone, mesterolone, methyltestosterone, testosterone and salts thereof
16.2.2 Anabolic steroids used it therapy: calusterone, nandrolone and salts thereof, dromostanolone, oxandrolone, ethylestrenol, oxymetholone, methandriol, stanozolol methandrostenolone, testolactone
16.2.3 Antiandrogens: cyproterone acetate
16.3 Estrogens
16.3.1 Estrogenic steroids used in therapy: diethylstilbestrol, estradiol, estriol, ethinylestradiol, mestranol, quinestrol
16.3.2 Anti-estrogens: chlorotrianisene, clomiphene, ethamoxytriphetol, nafoxidine, tamoxifen
16.4 Progestbins: allylestrenol, desogestrel, dimethisterone, dydrogesterone, ethinylestrenol, ethisterone, ethynadiol diacetate, etynodiol, hydroxyprogesterone, levonorgestrel, lynestrenol, medroxyprogesterone, megestrol acetate, norethindrone, norethisterone, norethynodrel, norgestrel, progesterone 17 Thyroid drugs 17.1 Thyroid drugs used in therapy: levothyronine, liothyronine 17.2 Anti-thyroid drugs used in therapy: carbimazole, methimazole, methylthiouracil, propylthiouracil When a hydrophobic drug, such as, for example, a steroid hormone is incorporated, preferably at least one hydrophobic antioxidant is present. Hydrophobic antioxidants which may be employed include, but are not limited to, tocopherols, such as $\alpha$-tocopherol, $\beta$-tocopherol, $\gamma$-tocopherol, $\delta$-tocopherol, $\epsilon$-tocopherol, $\zeta_1$-tocopherol, $\zeta_2$-tocopherol, and $\eta$-tocopherol; and 1-ascorbic acid 6-palmitate. Such hydrophobic antioxidants retard the degradation of the copolymer and retard the release of the biologically active agent. Thus, the use of a hydrophobic or lipophilic antioxidant is applicable particularly to the formation of loaded polymers which include drugs which tend to be released quickly, such as, for example, drug molecules having a molecular weight less than 500. The hydrophobic antioxidant(s) may be present in the loaded polymer in an amount of from about 0.1 wt. % to about 10 wt. % of the total weight of the polymer, preferably from about 0.5 wt. % to about 2 wt. %.

When the loaded polymer includes a hydrophilic drug, such as an aminoglycoside, the loaded polymer may also include, in addition to a hydrophobic antioxidant, a hydrophobic molecule such as cholesterol, ergosterol, lithocholic acid, cholic acid, dinosterol, betuline, or oleanolic acid, which may be employed in order to retard the release rate of the agent from the copolymer. Such hydrophobic molecules prevent water penetration into the loaded polymer, but do not compromise the degradability of the polymer matrix. In addition, such molecules have melting points from 150° C. to 200° C. or decreases the polymer matrix diffusion coefficient for the biologically active agent, such as drug molecule, to be released. Thus, such hydrophobic molecules provide for a more sustained release of a biologically active agent from the polymer matrix. The at least one hydrophobic molecule may be present in the loaded polymer in an amount of from about 0.1 wt. % to about 20 wt. %, preferably from 1.0 wt. % to 5.0 wt. %.

It is noted that, for the preparation of the water-in-oil emulsion according to the invention, it is necessary that a hydrophobic bioactive agent dissolves at least slightly in water, preferably at least to such an extent that the resultant loaded polymer comprises an amount of the bioactive agent which is sufficient to achieve a desired effect in vivo. If necessary, a surfactant may be added to the aqueous solution of the bioactive agent in order to achieve that a minimal desired amount of the bioactive agent is incorporated into the polymer. Examples of such surfactants are well known to the skilled artisan and may be used in amounts which can easily be optimized by the artisan based on his normal knowledge of the art. Specific examples of suitable surfactants include, but are not limited to, poly(vinyl) alcohol, Span 80, Tween and Pluronics.

The invention further requires the use of two solvents which are chosen to complement each other's action in the present process. The first solvent is to be chosen such that it is immiscible with water. In addition, the polymer which is to be loaded with bioactive agent(s) should be soluble in the first solvent. The second solvent is to be chosen such that the polymer is not soluble in it. Also, the first solvent is to be well miscible with the second solvent. Preferably, the first solvent mixes better with the second solvent than that the polymer dissolves in the first solvent. This ensures that, upon immersion of the water-in-oil emulsion in the second solvent, the first solvent will substantially completely migrate into the second solvent. Further preferred is that both solvents are immiscible with water. This makes it possible to prevent that the bioactive agent, which is processed in an aqueous solution, comes into contact with an organic solvent, which might be harmful to bioactive agent. Depending on the nature of the polymer to be loaded, the skilled person will be able to select suitable solvents. By way of example, good results have been obtained by using chloroform as the first solvent, and hexane as the second solvent when the polymer is polyethylene glycol terephtalate/polybutylene terephthalate copolymer.

In a first step of the present process, a solution is provided of the polymer in the first solvent. The concentration of this solution is not critical. On the one hand, it is important that all of the polymer dissolves. On the other hand, it is preferred that the amount of the first solvent used is kept as small as possible in order to keep the process efficient.

Of the polymer solution, a water-in-oil emulsion is prepared by mixing it with an aqueous solution of the bioactive agent(s),. Under certain circumstances, it may be desired to add conventional stabilizers for enhancing the stability of the water-in-oil emulsion. Typical examples of such stabilizers include proteins such as albumin or casein, Pluronics and Span 80. It is, however, preferred that such stabilizers are not used.

The amount of bioactive agent(s), in the aqueous solution will be chosen such that a desired amount of these bioactive agents is eventually incorporated into the polymer. Depending on the type of polymer and the nature of the bioactive agent(s), the amount of incorporated agent may vary. For proteins and peptides, for example, it has been found that various proteins and peptides can be incorporated into the polymer in concentrations up to 10 wt. %, based on the weight of the loaded polymer. When using particularly hydrophilic bioactive agents, such as the protein leuprolide, it has even been found possible to incorporate the agent into the polymer in a concentration of up to 50 wt. %, based on the weight of the loaded polymer. The lower limit of the amount of bioactive agent(s), is not critical and will depend on the activity of the bioactive agent(s), and on the envisaged application of bioactive agent loaded polymer. In the case of proteins and peptides typically, at least 0.01 wt. %, based on the weight of the loaded polymer, of protein and/or peptide will be incorporated.

The amount of water used for preparing the aqueous bioactive agent solution will be at least so high as to enable an efficient dissolution of the bioactive agent without employing unduly harsh conditions that might adversely affect the stability and/or biological activity of the bioactive agent. The upper limit of the amount of water used will depend on the rate at which the bioactive agent is to be released from the polymer in a final, envisaged application of the bioactive agent loaded polymer. It has been found that the use of larger amounts of water, leads to higher release rates of the polymer. Typically, the aqueous solution of the bioactive agent(s) will comprise between 0.001 and 10 wt. % of bioactive agent(s), based on the weight of the solution. In practice, the amount of bioactive agents in the solution will depend on the solubility of the bioactive agents and on the stability of the water-in-oil emulsion.

The obtained water-in-oil emulsion is next immersed in the second solvent by injection through a nozzle. The diameter and shape of the nozzle can be varied to obtain fibers of different thickness and shape. The injection itself will usually be driven by a pressure by virtue of which the emulsion is transported through the nozzle into the second solvent. The injection may for instance be accomplished by use of a syringe or an extruder. The amount of the second solvent is not critical. It should be at least sufficient for the emulsion to be completely immersed in it and to allow a substantially complete migration of the first solvent from the emulsion into the second solvent. The upper limit will generally chosen on the basis of economic considerations.

Upon immersion of the emulsion into the second solvent, due to the specific selection of the first and second solvents, the first solvent will migrate from the emulsion into the second solvent. In practice, it may often be observed that first exchange of the first and second solvents takes place, before the first solvent will migrate into the second solvent. This may have the effect that the polymer fibers are provided with a porosity. This phenomenon and how it may be controlled to obtain a desired porosity has been described by P. van de Witte, "Polylactide membranes. Correlation between phase transitions and morphology", PhD thesis, University of Twente, Enschede, 1994.

As a result, the polymer, which does not dissolve in the second solvent, will solidify thereby incorporating the bioactive agent(s). Finally, the solid loaded polymer may be removed from the mixture of first and second solvents in any conventional manner and may eventually be dried.

In a preferred embodiment, the obtained fibers may be formed into a fibrous mesh by collecting the fibers in a mold, and bonding them together by use of a suitable solvent mixture. This mixture should comprise at least one solvent in which the polymer dissolves and at least one solvent in which the polymer does not dissolve. Preferably, a mixture is used of the above described first and second solvents. The second solvent will generally be present in an amount exceeding that of the first solvent, in order to avoid the risk of any of the polymer dissolving in the solvent mixture. Preferably, the volumetric ratio of the first solvent to the second solvent lies between 1:1 and 1:3.

It will be understood that the invention also encompasses a bioactive agent loaded polymer obtainable by the process as set forth herein above. Said polymer loaded with one or more bioactive agents may be used in biological, pharmaceutical and surgical applications, wherein a (controlled) release of a bioactive agent(s) from a polymeric substrate is desired. Examples of such applications include, but are not limited to, carriers for controlled drug release and scaffolds for tissue engineering.

The invention will now be elucidated by the following, non-restrictive examples.

EXAMPLES

Materials and Methods

Materials

Poly (ethylene glycol)terephthalate/poly(butylene terephthalate) multiblock copolymers (PEG/PBT) were obtained from IsoTis BV, Bilthoven, The Netherlands. The copolymers contained 30 wt % PBT and the PEG segment length was 1000 g/mole (1000PEG70PBT30). Phosphate buffered saline (PBS), pH 7.4 was purchased from NPBI (Emmercompascuum, The Netherlands). Bovine serum albumin (BSA, heat shock fractionate, fraction V powder minimum 98%) was purchased from Sigma Chem. Corp. (St. Louis, USA). All solvents used were of analytical grade.

Preparation of Bioactive Agent Loaded PEG/PBT Fiber Meshes

The bioactive agent in this example was a protein. Protein loaded PEG/PBT fibers were prepared from water-in-oil emulsions. To produce such emulsions, 3 or 3.5 ml of a protein solution in PBS (containing 25 mg/ml BSA) was emulsified in a solution of 2 g PEG/PBT in 14 ml $CHCl_3$ using ultra-turrax-mixing (30 s at 20.5 krpm, Ika Labortechnik T25). Subsequently, the emulsion was poured into a 20 ml glass syringe (Becton Dickinson Multifit) equipped with a 0.4 mm needle (Neolus Terumo 12G×1.5"). The emulsion was pushed through the needle into a beaker containing 21 hexane at a speed of 0.5 ml/min. by means of a perfusion pump (Secura E, B. Braun). The hexane bath was stirred at 300 rpm. to prevent premature sticking of the fibers. After fiber formation was completed, the fibers were collected and transferred to a glass mold of the desired shape (cylindrical, 5 cm diameter and 1.7 cm height). To bond the fibers, a mixture of hexane and $CHCl_3$ (7:3, 3:2, or 1:1, v/v) was introduced into the mold. After drying overnight under atmospheric conditions, the fiber structures were freeze dried for 3 days, and stored at −40° C.

Scanning Electron Microscopy (SEM)

A Hitachi S-800 field emission SEM was used to evaluate the surface characteristics and internal structure of fibrous scaffolds. The devices were cut in liquid nitrogen and mounted on a substrate holder. Samples were sputter-coated with a thin gold layer.

In vitro Release of Bioactive Agent

Protein loaded fiber meshes (approximately 40 mg) were incubated in 5 ml PBS (pH 7.4). Vials were continuously shaken at 37° C. and samples were taken at various time points. Protein content was determined using a standard Coomassie Blue assay (Pierce). Buffer was refreshed after sampling.

Results and Discussion

Matrix Characterization

Bonded fiber meshes, containing BSA, were prepared in a three-step procedure. First, a water-in-oil emulsion was formed from an aqueous protein solution and a polymer solution in CHCl3. The second step involves wet spinning of the w/o emulsion into a hexane bath. Hexane is miscible with $CHCl_3$, but is a non-solvent for the PEG/PBT copolymers. Consequently, extrusion of the fibers into hexane results in solidification of the fibers, due to exchange of solvent and non-solvent. Since hexane is not miscible with water, contact between the incorporated proteins and hexane is prevented as much as possible.

Figure 1B:
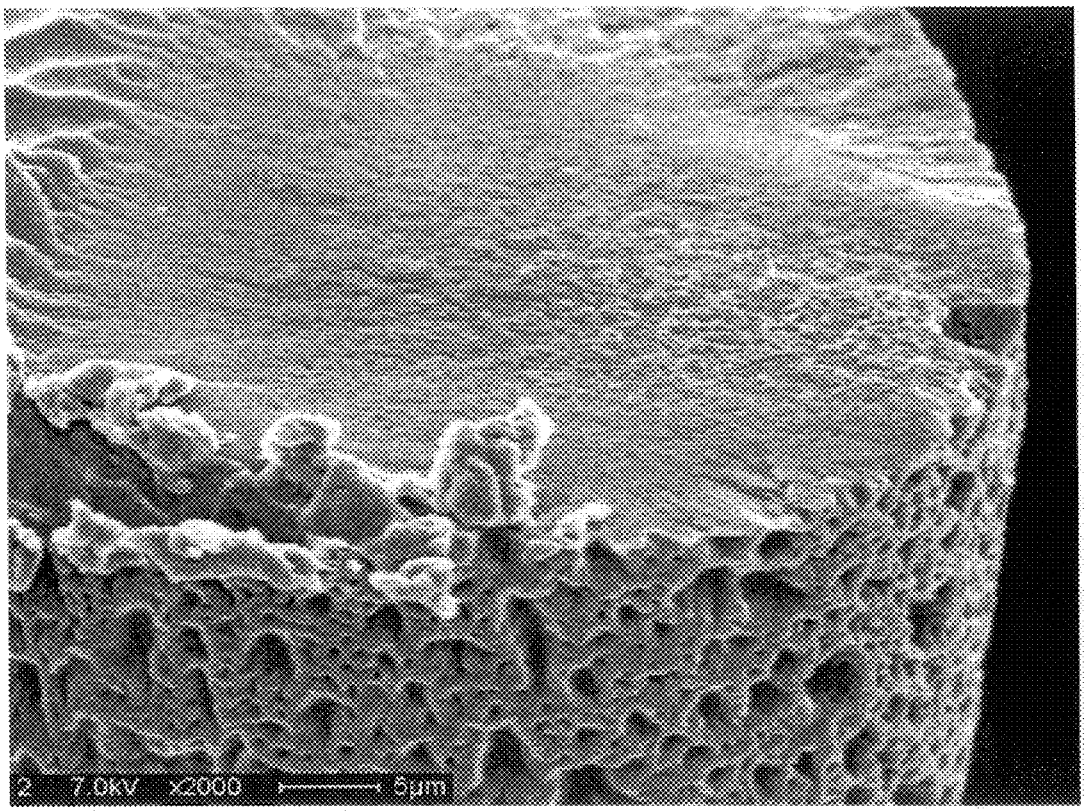

FIG. 1 shows scanning electron micrographs of a cross-section of the obtained protein loaded PEG/PBT fibers (magnification is 500× (A) or 200× (B)). The fiber cross-section was not circular (FIG. 1a). This is probably caused by the shape of the needle. The surface of the fibers was porous, whereas the interior of the fibers seemed to be dense. This is in contrast with the morphology of protein loaded PEG/PBT matrices, prepared by immersion precipitation of w/o emulsion droplets in hexane. These structures showed a porous internal morphology (data not shown). Probably, the morphology of the fibers was changed during the fiber bonding step in the solvent/non-solvent mixture. Furthermore, it cannot be excluded that the internal structure of the fibers as shown in FIG. 1 was affected by the cutting procedure, used to obtain cross-sections for scanning electron microscopy.

In order to be used for tissue engineering applications, fiber meshes must often be configured in a certain shape and immobilized. This can be achieved by collecting the fibers in a mold, followed by bonding in a solvent-non-solvent mixture. The efficiency of this fiber bonding process was dependent on the solvent to non-solvent ratio of the $CHCl_3$/hexane mixture. Immersion of the fiber meshes in mixtures with a $CHCl_3$ to hexane ratio of 3:7 (v/v) did not result in stable structures. Improved bonding was obtained for devices immersed in a solvent/non-solvent mixture with a composition of 2:3. Such bonded fiber structures were stable for several days in PBS buffer at 37° C. in a shaking bath. A bonded fiber mesh, prepared by immersion in $CHCl_3$/hexane 1:1, remained intact for over 50 days of continuously shaking at 37° C. Solvent/non-solvent mixtures containing over 50% (v/v) $CHCl_3$ could not be used, since the fibers dissolved in such mixtures.

FIG. 2 shows scanning electron micrographs of the structure of the obtained protein loaded PEG/PBT fiber meshes (cross-section (A, C) and surface morphology (B, D) of fibers, bonded in a mixture of $CHCl_3$ and hexane with a volume ratio 3:7 (A, B) or 1:1 (C, D)).

Figure 2A:
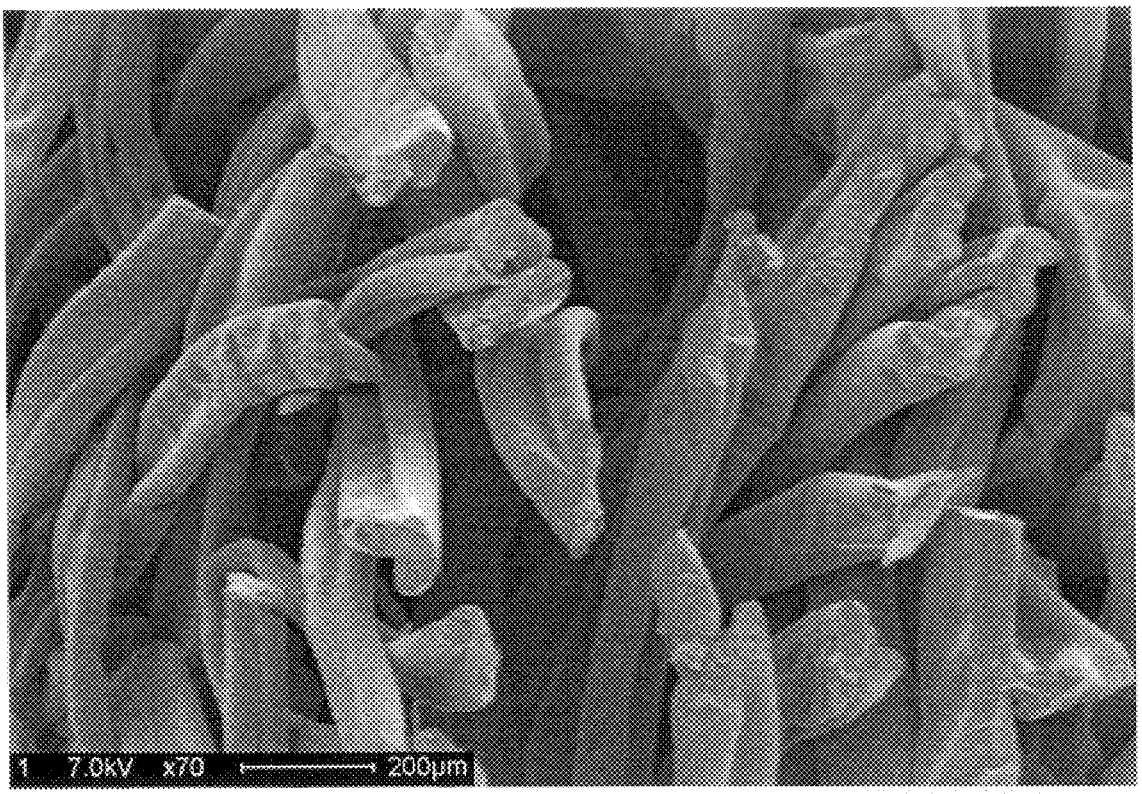
FIGS. 2A–2D depict scum electron micrographs of the structure of structure of protein loaded PEG/PBT fiber meshes. (A) and (C) depict cross sections. (B) and (D) depict surface morphology.
Figure 2B:
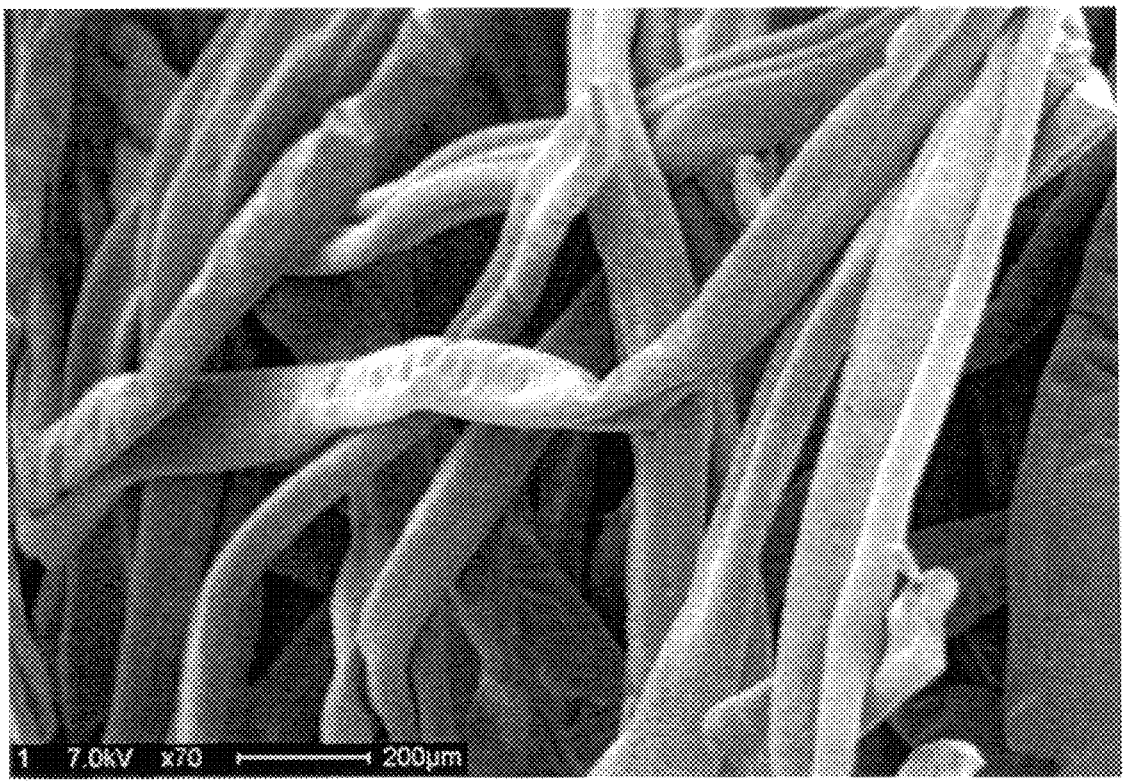
Figure 2C:
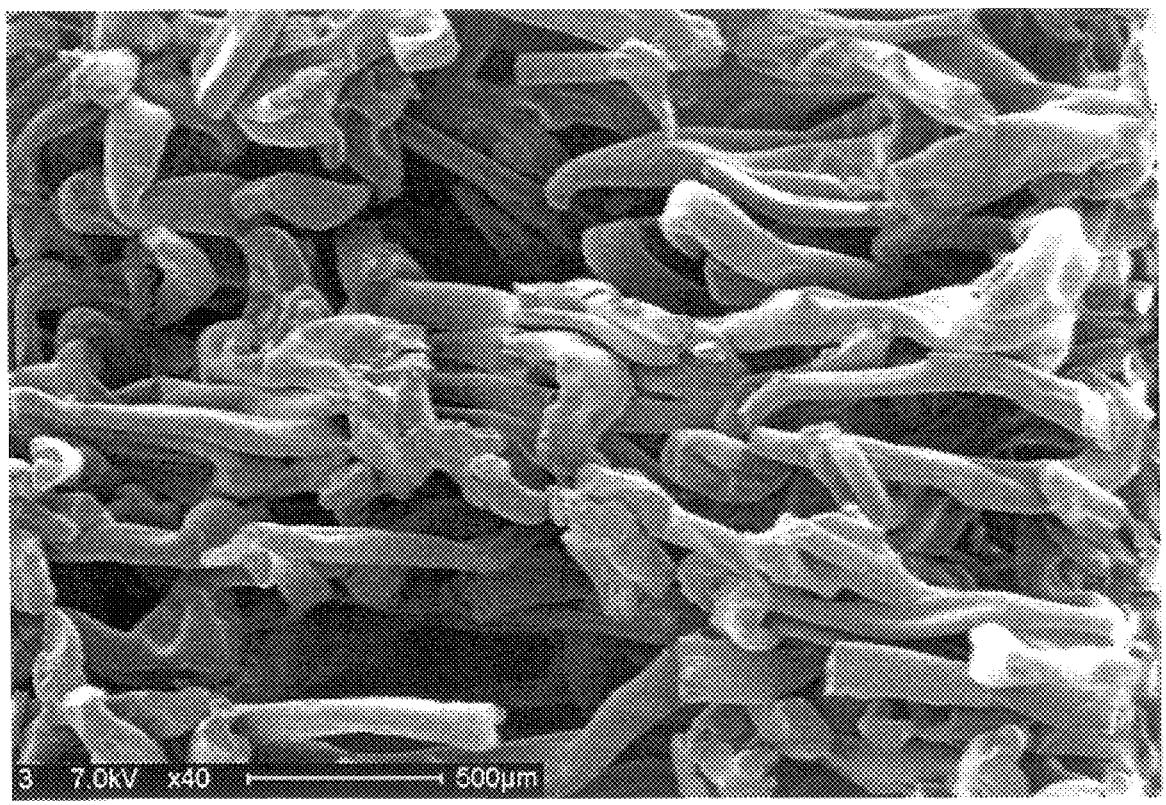
Figure 2D:
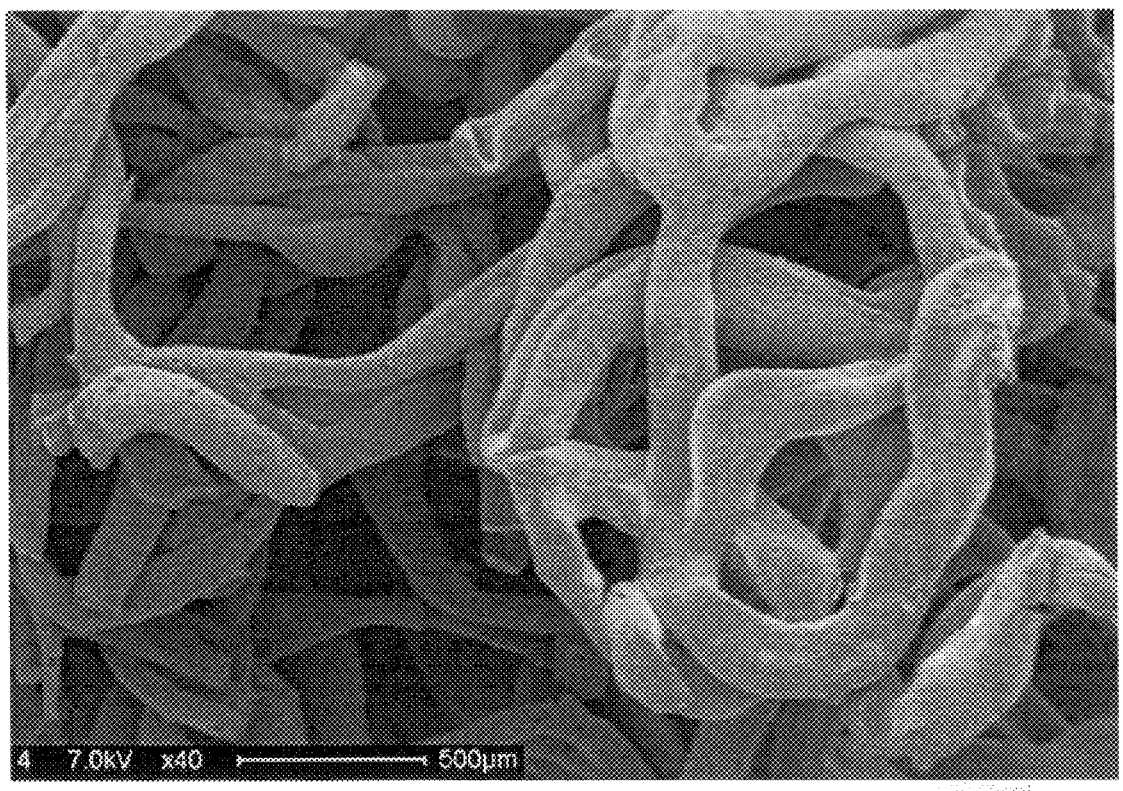
Figure 3:
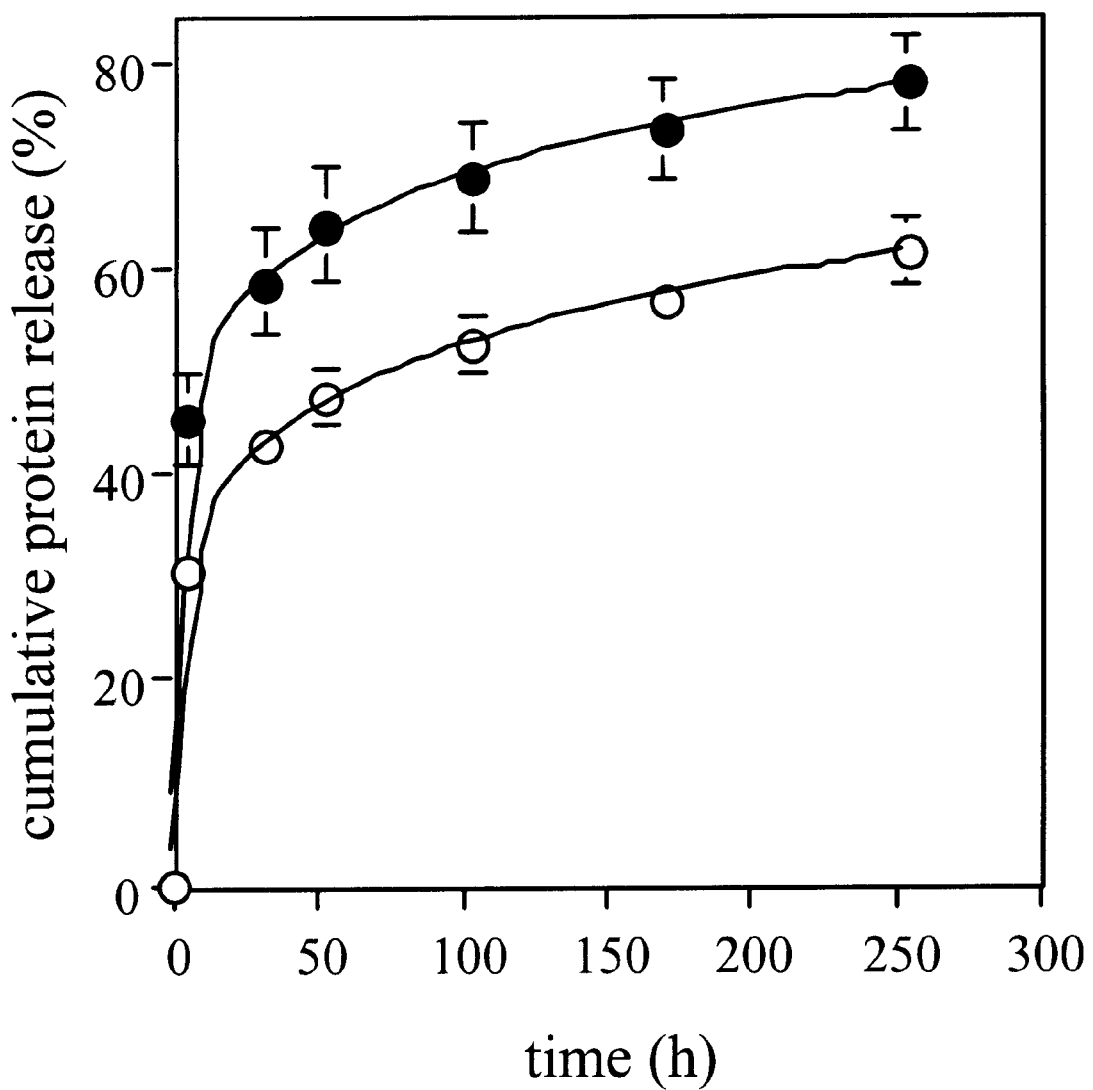
FIG. 3 graphically depicts the total protein release from bonded fiber meshes.

As shown in FIG. 2D, confluency was observed for the structures bonded in $CHCl_3$/hexane 1:1 (v/v), whereas such connections were scarcely found for meshes immersed in solvent/non-solvent mixtures with a composition of 3:7 or 2:3 (FIG. 2B).

Bioactive Agent Release From Bonded Fiber Meshes

Two different fiber meshes were selected to study bioactive agent release in phosphate buffered saline (PBS). The fibrous structures were bonded in a mixture of hexane and $CHCl_3$ of volume ratio 1:1. In order to modulate the bioactive agent release rate, the composition of the w/o emulsion which was used to produce the loaded fibers, was varied. Previous experiments have shown that the water content in the w/o emulsion is a powerful tool to manipulate the release rate of high molecular weight proteins. In the present, devices were prepared from emulsions which contained a protein as the bioactive agent, in a concentration of 1.5 or 1.75 ml of a protein solution per g of polymer, respectively.

The total protein release from the bonded fiber meshes is presented in FIG. 3 (protein release from PEG/PBT fiber meshes, bonded in a mixture of hexane and $CHCl_3$ (1:1, v/v): the devices were prepared from emulsions which contained 1.5 (open symbols) or 1.75 ml (closed symbols) protein solution per g of polymer (n=3; ±s.d.).). For both devices, a relatively large amount of protein was released during the first hours of incubation in the buffer. Thereafter, a slow release was observed, for a period longer than 10 days. A higher protein release rate was found for the device prepared from the emulsion which contained the highest water content.

What is claimed is:

1. A process for preparing an implant for controlled release of a bioactive agent in vivo arising a polymer fiber loaded with one or more bioactive agents, said process comprising a wet spinning technique having the steps of:

a) providing a solution of a biocompatible and biodegradable amphiphilic block copolymer comprising hydrophilic blocks and hydrophobic blocks in a first solvent immiscible with water;

b) adding an aqueous solution of the bioactive agent to the amphiphilic block copolymer solution to form an emulsion;

c) immersing the emulsion in a second solvent miscible with the first solvent and in which the amphiphilic block copolymer is essentially insoluble by injecting the emulsion through a nozzle into the second solvent;

d) allowing the first solvent to migrate into the second solvent to form a solid amphiphilic block copolymer fiber loaded with the bioactive agent, wherein water content of the aqueous solution in step (b) affects a rate of release of the bioactive agent in vivo: and e) shaping the amphiphilic block copolymer fiber into an implant.

2. The process according to claim 1, wherein the hydrophilic blocks comprise polyalkylene glycol and the hydrophobic blocks comprise an aromatic ester.

3. The process according to claim 1, wherein the bioactive agent is selected from the group consisting of antimicrobial agents, anti-viral agents, anti-tumor agents, immunogenic agents, lipids, lipopolysaccharides, hormones and growth factors.

4. The process according to claim 1, wherein the bioactive agent is selected from the group consisting of peptides, oligopeptides, polypeptides and proteins.

5. The process according to claim 1, wherein the first solvent has a greater solubility in the second solvent when the polymer is dissolved in the first solvent.

6. An implant loaded with one or more bioactive agents prepared according to the process of claim 1.

7. The implant according to claim 6, wherein said bioactive agent is a peptide, oligopeptide, polypeptide or protein.

* * * * *